US00PP10331P

United States Patent [19]

VandenBerg

[11] Patent Number: Plant 10,331

[45] Date of Patent: Apr. 14, 1998

[54] CHRYSANTHEMUM PLANT NAMED 'PILAR'

[75] Inventor: Cornelis P. VandenBerg, Salinas, Calif.

[73] Assignee: Yoder Brothers, Inc., Barberton, Ohio

[21] Appl. No.: 812,147

[22] Filed: Mar. 6, 1997

[51] Int. Cl.[6] ..... A01H 5/00

[52] U.S. Cl. ..... Plt./74.1

[58] Field of Search ..... Plt./74.1, 76

*Primary Examiner*—Howard J. Locker

*Attorney, Agent, or Firm*—C. A. Whealy

[57] ABSTRACT

A distinct cultivar of Chrysanthemum plant named 'Pilar', characterized by its anemone spray-type inflorescences that are about 6.5 cm in diameter; attractive purple ray florets with yellow-tipped disc florets; numerous inflorescences per flowering stem; numerous ray and disc florets per inflorescence; and excellent postproduction longevity with flowering stems maintaining good substance and color for at three or four weeks in an interior environment after one week of cool storage.

3 Drawing Sheets

The present invention relates to a new and distinct cultivar of Chrysanthemum plant, botanically known as *Dendranthema grandiflora* and referred to by the cultivar name Pilar.

The new cultivar is a product of a planned breeding program conducted by the inventor in Salinas, Calif. The objective of the breeding program is to create new Chrysanthemum cultivars having inflorescences with desirable colors and good form and substance.

The new cultivar originated from a cross made by the inventor in November, 1991, in Salinas, Calif. of the commercial cultivar Effect (disclosed in U.S. Plant Pat. No. 8,935) as the female, or seed, parent with an unnamed proprietary seedling selection as the male, or pollen, parent. The female parent, the commercial cultivar Effect is a anemone spray-type cut Chrysanthemum with light purple ray florets and yellow-green disc florets. The male parent, seedling number 0356, is a daisy spray-type cut Chrysanthemum with light pink ray florets.

The cultivar Pilar was discovered and selected by the inventor as a flowering plant within the progeny of the stated cross in a controlled environment in Salinas, Calif. on Apr. 5, 1993. The selection of this plant was based on its desirable inflorescence color and good form and substance.

Asexual reproduction of the new cultivar by terminal cuttings taken in a controlled environment in Salinas, Calif., has shown that the unique features of this new Chrysanthemum are stable and reproduced true to type in successive generations.

The cultivar Pilar has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pilar'. These characteristics in combination distinguish 'Pilar' as a new and distinct cultivar:

1. Anemone spray-type inflorescences that are about 6.5 cm in diameter.
2. Attractive purple ray florets with yellow-tipped disc florets.
3. Numerous inflorescences per stem.
4. Numerous ray and disc florets per inflorescence.
5. Excellent postproduction longevity with flowering stems maintaining good substance and color for at three or four weeks in an interior environment after one week of cool storage.

The accompanying colored photographs illustrate the overall appearance of the new cultivar, showing the colors as true as it is reasonably possible to obtain in colored reproductions of this type.

The first photograph comprises a side perspective view of a typical flowering stem of 'Pilar' grown as a single stem spray cut Chrysanthemum.

The second photograph comprises a side perspective view of typical inflorescences of the cultivar Pilar.

The third photograph comprises a top perspective view of adaxial (left) and abaxial (right) surfaces of typical inflorescences of the cultivar Pilar.

The fourth photograph comprises a top perspective view of the adaxial (bottom of photograph) and abaxial (top of photograph) surfaces of leaves of the cultivar Pilar at two different stages of development showing the differences in size and lobation development. Floret and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse. Rooted cuttings were planted Nov. 7, 1996 and cut flowers were harvested on Jan. 13, 1997. After planting rooted cuttings of the new cultivar, plants received three weeks of long day/short nights following by short day/long nights until flowering. Measurements and numerical values represent averages for six typical flowering stems.

Botanical classification: *Dendranthema grandiflora* cultivar Pilar.

Commerical classification: Anemone spray-type cut Chrysanthemum.

Parentage:

*Male or pollen parent.*—Unnamed proprietary *Dendranthema grandiflora* seedling selection number 0356.

*Female or seed parent.*—*Dendranthema grandiflora* cultivar Effect (disclosed in U.S. Plant Pat. No. 8,935).

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous anemone spray-type cut flower. Stems upright, uniform habit and freely branching.

*Flowering stem length.*—About 86 cm.

*Foliage description.*—Leaf arrangement: Alternate. Leaf size, fully expanded: Length: About 12 cm. Width: About 7.75 cm. Leaf apex: Cuspidate. Leaf base: Attenuate. Leaf margin: Deeply lobed. Leaf texture: Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation adaxial surface: 147B. Venation abaxial surface: 147B. Petiole: Length: About 2.5 cm. Color: 147B.

Flowering description:

*Appearance.*—Anemone-type inflorescence form. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 53 days later.

*Postproduction longevity.*—In an interior environment, flowering stems will maintain good color and substance for at three or four weeks in an interior environment after one week of cool storage.

*Quantity of inflorescences.*—About 10 inflorescences per flowering stem.

*Inflorescence size.*—Diameter: About 6.5 cm. Depth (height): About 1.5 cm. Diameter of disc: About 4 cm.

*Ray florets.*—Shape: Elliptic. Size: Length: About 3.2 cm. Width: About 8 mm. Apex: Rounded. Base: Attenuate. Margin: Entire. Texture: Satiny, smooth, glabrous. Aspect: Mostly flat to slightly cupped. Number of ray florets per inflorescence: About 52. Color: When opening: Adaxial surface: 82B/82C. Abaxial surface: 84B. Mature: Adaxial surface: 82C. Abaxial surface: 84B/84C.

*Disc florets.*—Shape: Tubular during early development becoming oblanceolate to spatulate with further development. Apex: Dentate. Size (largest): Length: About 1.8 cm. Width: Apex: About 6 mm. Base: About 1 mm. Number of disc florets per inflorescence: About 170. Color: Immature: Apex: 154A to 5A. Base: White. Mature: Tube: Apex: 5A. Mid-section: 82C. Base: White. Throat: Apex: 82B. Base: White.

*Peduncle.*—Aspect: Strong and angled about 55° to the stem. Length: First peduncle: About 4.25 cm. Fourth peduncle: About 7 cm. Seventh peduncle: About 9.25 cm. Texture: Slightly pubescent. Color: 147B.

*Reproductive organs.*—Androecium: Present on disc florets only. Anther color: 9A. Pollen: Moderate, 9A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Pilar', as illustrated and described.

* * * * *

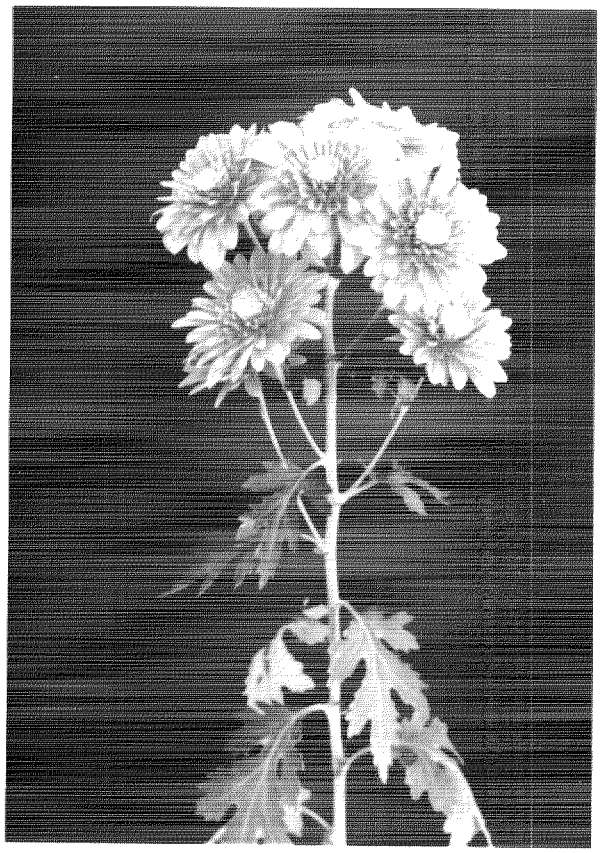

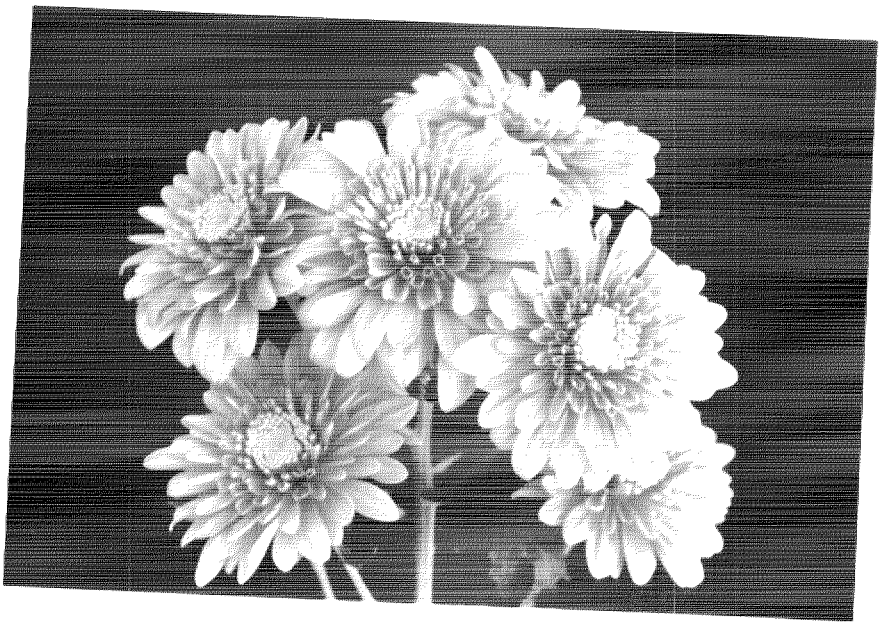

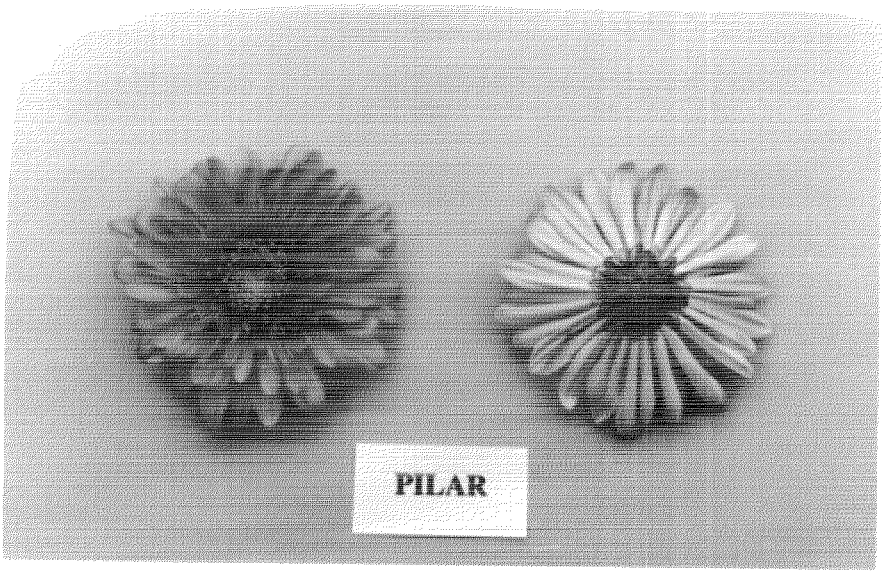
PILAR
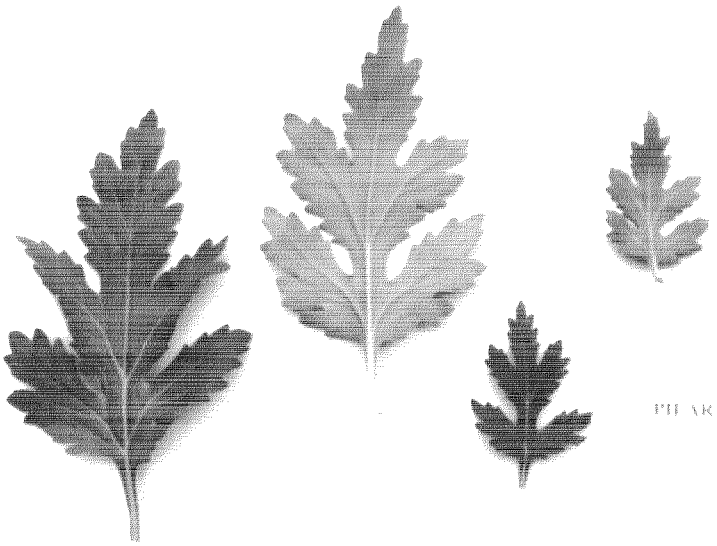
PILAR